United States Patent [19]

Findlay et al.

[11] Patent Number: 4,564,685
[45] Date of Patent: Jan. 14, 1986

[54] DIPHENYLMETHANE COMPOUNDS

[76] Inventors: John W. A. Findlay, Rte. 2, Box 514, Chapel Hill, N.C. 27514; Geoffrey G. Coker, 80 Pickhurst Park, Bromley, Kent, England

[21] Appl. No.: 474,729

[22] Filed: Mar. 10, 1983

[51] Int. Cl.[4] ............... C07C 53/132; C07D 207/04; C07D 211/06; C07D 295/00
[52] U.S. Cl. .................... 548/578; 260/404; 544/171; 544/172; 546/239; 560/37; 562/441
[58] Field of Search ............... 548/572, 578; 562/441; 542/468, 469; 424/274; 560/37; 514/539, 567, 408, 317, 236, 233; 544/171-172; 546/239

[56] References Cited

U.S. PATENT DOCUMENTS

| | | | |
|---|---|---|---|
| 2,567,245 | 9/1951 | Sperber et al. | 546/333 |
| 3,370,058 | 2/1968 | Judd et al. | 548/578 X |
| 3,766,174 | 10/1973 | Nakanishi et al. | 542/468 |
| 3,862,173 | 1/1975 | Carr et al. | 542/469 X |
| 3,965,181 | 6/1976 | Marx | 542/468 X |
| 4,028,352 | 6/1977 | Cavalla et al. | 542/469 X |
| 4,307,245 | 12/1981 | Hu et al. | 560/37 X |
| 4,355,036 | 10/1982 | Villani | 424/267 |
| 4,501,893 | 2/1985 | Findlay et al. | 546/281 |

FOREIGN PATENT DOCUMENTS 1227464 10/1966 Fed. Rep. of Germany .
807757 1/1959 United Kingdom .

OTHER PUBLICATIONS

Kuntzman, et al.; C.A. 71 (1969), 11415f.
Buzas; J. Med. Chem. (1980), 23, pp. 149-153.
Hucker, et al.; Drug Metabolism & Disposition, (1981), vol. 9, pp. 428-433.
ASPET (1980), Findlay Abstract.
Physician's Desk Reference (PDR), 1978, pp. 708 & 707.

Primary Examiner—Joseph Paul Brust
Attorney, Agent, or Firm—Donald Brown

[57] ABSTRACT

This disclosure describes compounds of Formula I.

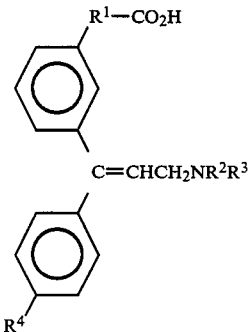

(including their pharmaceutically acceptable salts and esters) which have potent antihistamine activity which are substantially free from sedative effects.

12 Claims, No Drawings

DIPHENYLMETHANE COMPOUNDS

The present invention relates to new chemical compounds exhibiting antihistamine activity, to processes for preparing them, to novel intermediates involved in their preparation, to pharmaceutical compositions containing them and to their use in medicine.

The antihistamines now in use, eg. diphenhydramine, the pheniramines, pyrilamine, promethazine and triprolidine may cause sedation or drowsiness in some patients. (L. Goodman and A. Gilman, *The Pharmacological Basis of Therapeutics*, 4th ed., p. 640, Macmillan, New York, 1970). This sedating effect limits the use of antihistamines by patients who must operate machinery, drive motor vehicles or must engage in activities requiring mental alertness.

A novel group of compounds having potent antihistamine activity which are substantially free from sedative effects has now been discovered.

Accordingly this invention provides the compounds of formula I.

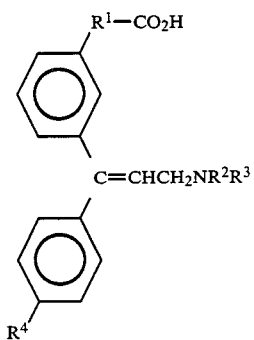

wherein $R^1$ is $(CH_2)_n$, n is an integer 1 to 7, or $(CH_2)_a CH:CH—(CH_2)_b$, a and b are independently 0 to 5 and the sum of a and b does not exceed 5. $R^2$ and $R^3$ are the same or different and can be hydrogen, lower alkyl (1 to 4 carbons) or taken together with the nitrogen comprise a nitrogen containing heterocyclic ring (of four to six ring member) such as pyrrolidino, piperidino or morpholino. $R^4$ is hydrogen, halogen such as Br or Cl, lower alkyl (1 to 4 carbons) or lower alkoxy (1 to 4 carbons).

This invention also includes ester and amide derivatives as well as acid addition salts and salts of the carboxylic acid group the compounds of formula (I).

Of the compounds of formula (I) those of formula (IA) are preferred.

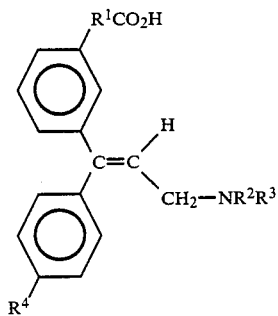

wherein $R^1$ is $(CH_2)_0$, i.e. a bond, $(CH_2)_2$ or CH=CH, $NR^2R^3$ is pyrrolidino or dimethylamino and $R^4$ is the same as for formula (I).

The compounds of formula (IA) which were found to be particularly active are:

3-(3-pyrrolidino-1-(4-tolyl)prop-1E-enyl)benzoic acid (E)-3-(3-pyrrolidino-1-(4-tolyl)prop-1E-enyl)cinnamic acid (E)-3-(3-pyrrolidino-1-(4-methoxyphenyl)prop-1E-enyl))cinnamic acid (E)-3-(3-dimethylamino-1-(4-tolyl)prop-1-E-enyl))cinnamic acid 3-(3-(3-pyrrolidino-1-(4-tolyl)prop-1-E-enyl)phenyl))-propionic acid Compounds of formula (I) and their salts may be synthesized by methods known in the art for the synthesis of compounds having analogous structures.

1. A method for preparing compounds of formula (I) comprises reacting a compound of (II) with a compound of formula (III) by the Wittig method (see *Organic Reactions*, 14, 270–490 (1965) and *Pure and Applied Chemistry*, 9, 245–254 (1964)).

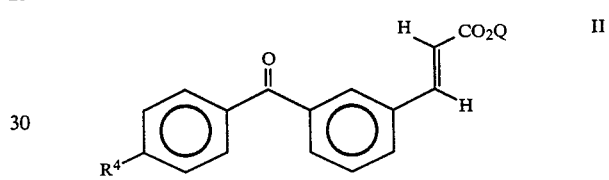

$$(R^5)_3P=CHCH_2NR^2R^3 \qquad III$$

wherein $R^1$, $R^2$, $R^3$ and $R^4$ are the same as defined for formula (I), $R^5$ is aryl such as phenyl or lower alkyl (1 to 4 carbons) and Q is a lower alkyl group (1–4 carbons) or an alkali metal such as sodium or alkali earth metal such as lithium. The reaction may be followed by deprotection of the carboxyl group as necessary. The product may be converted to an acid addition salt, a salt of the carboxylic acid, an ester or an amide by conventional methods.

The compound of formula (III) is a Wittig reagent which may be prepared by treatment of a phosphonium salt (IV) with a strong base, for example an alkyl or aryl lithium compound or sodium hydride in a suitable solvent, for example toluene or tetrahydrofuran.

$$(R^5)_3P^+CH_2CH_2NR^2R^3 \qquad IV$$

wherein $R^2$ and $R^3$ are as defined above and $R^5$ is lower alkyl or phenyl.

The phosphonium salts (IV) are prepared by known methods (e.g., see British Pat. No. 1, 161, 201).

Compounds of formula (II) in which $R^1$ is —CH=CH— (trans) may be prepared by reacting a compound of formula (V) with an acrylate ester (VI) in presence of a catalyst consisting of palladium acetate and a triarylphosphine and a tertiary amine such as triethylamine or tributylamine. Optionally a solvent such as acetonitrile may be used and the reactants may with advantage be heated together in a sealed pressure vessel (e.g., see R. F. Heck et al., *J. Org. Chem.*, 43, 2947 (1978)).

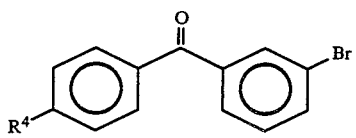 V

 VI wherein $R^4$ is as defined above and $R^6$ is a lower alkyl group (1–4 carbon atoms).

Compounds of formula (II) may also be prepared by reacting a compound of formula (VII):

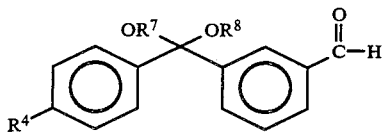 VII wherein $R^7$ and $R^8$ may be the same or different and are lower alkyl, or may together form a cyclic ketal, with malonic acid in the presence of a pyridine and piperidine, or with a Wittig reagent prepared by treating a phosphonium salt (VIII A) or a phosphonate ester (VIII B) with a suitable base in an appropriate solvent:

 VIII A

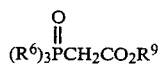 VIIIB wherein $R^5$ and $R^6$ are as defined above, m is 1 to 6 and $R^9$ is lower alkoxy. The ketone (II) is generated by acidic hydrolysis of the protecting ketal. The double bond in the group $R^1$ may be reduced if desired with hydrogen in presence of a catalyst such as palladium charcoal.

Compounds of formula (VII) may be prepared from compounds of formula (V) by conversion to a ketal by reaction with a mono or dihydroxy compound in presence of an acid catalyst followed by reaction with a metal alkyl compound for example butyllithium and subsequent treatment with dimethylformamide. The reaction is preferably conducted at low temperature (below $-60°$) in a solvent such as toluene.

In turn compounds of formula (V) can be prepared by treatment of a compound of formula (IX) with a metal alkyl compound, for example butyllithium in a suitable solvent such as toluene, followed by reaction with a compound of formula (X)

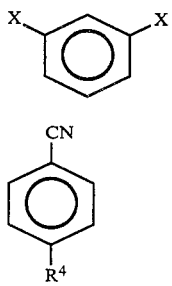 IX

X wherein X is halogen such as Cl or Br and $R^4$ is defined as above. 2. Compounds of formula (I) may also be synthesized by reacting compounds of formula (XI)

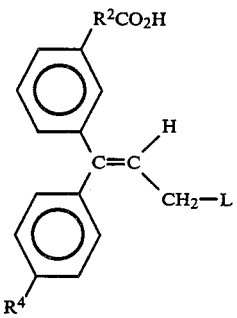 XI wherein L is a leaving group as defined by J. March, *Advanced Organic Chemistry*, 2nd ed., pages 683 and 895, McGraw Hill, New York, 1977, e.g., —Br, —Cl, toluene sulfonate, etc.

with compounds of formula (XII)

$HNR^2R^3$ XII wherein $R^2$ and $R^3$ are defined for compounds of formula (I)

3. A further method for synthesis of compound of formula (I) comprises dehydration of compounds of formula (XIII).

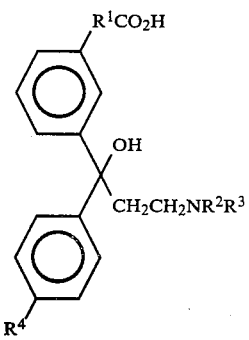 XIII wherein $R^1, R^2, R^3$ and $R^4$ are as defined for compounds of formula (I)

Compounds of this invention have the same utilities as antihistamines used clinically at present. They bind competitively to the $H_1$ histamine receptor site. They may be used to relieve symptoms of nasal stuffness due to colds and vasomotor rhinitis and for the symptomatic control of all allergic conditions including nasal allergy, perennial rhinitis, urticaria, angioneurotic oedema, allergic conjunctivitis, food allergy, drug and serum reactions, insect bites and stings and desensitizing reactions. The compounds are also indicated in all conditions responsive to its antipuritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compounds of this invention are not sedating and have little or no anticholinergic side effects.

The amount of active compound required for use in the above conditions will vary both with the route of administration, the condition under treatment and the mammal undergoing treatment, and is ultimately at the discretion of the physician. A suitable oral dose of the active compound for a mammal is in the range of from 0.025 to 1.0 mg per kilogram body weight per day; preferably from 0.04 to 0.24 mg/kg. For example a typical dose for a human recipient of compound (A) is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical sub-dose (which can be given in a pharmaceutical formulation such as a tablet, capsule or syrup) of the active compound for a human recipient is about 2 mg.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, phosphoric, maleic, salicylic, p-toluenesulfonic, tartaric, citric, methanesulfonic, formic, malonic, succinic, naphthalene-2-sulfonic and benzenesulfonic. Also pharmaceutically acceptable salts can be prepared as alkaline metal or alkaline earth salts, such as sodium, potassium or calcium salts of the carboxylic acid group.

The following Examples are provided by the way of illustration of the present invention and should in no way be construed as a limitation thereof. All temperature indicated are in degrees Celsius.

EXAMPLE 1

(E)-3-(3-Pyrrolidino-1-(4-tolyl)prop-1E-enylbenzoic acid

To a stirred and cooled suspension of triphenyl-2-pyrrolidinoethylphosphonium bromide (17.6 g) in tetrahydrofuran (96 mL) was added a solution of butyl lithium in hexane (28 mL, 1.6M) in portions, the temperature being kept at 0°. After a further 30 minutes' stirring at 0°, a solution of 3-methoxycarbonyl-4'-methylbenzophenone (Smith, *J. Amer. Chem. Soc.*, 1921,) (10.16 g)

in tetrahydrofuran (50 mL) was added dropwise, and the mixture was allowed to come to room temperature and then heated at 55° for 18 hours. Most of the tetrahydrofuran was evaporated in vacuo, water and dilute hydrochloric acid were added and the mixture was washed with ether. The clear aqueous solution was basified with 2N-sodium carbonate solution and the precipitated oil was extracted with ether. Purification by chromatography on a column of silica with a chloroform-methanol (50:1) mixture as eluant gave a mixture of the (E)- and (Z)-forms of methyl 3-(3-pyrrolidino-1-(4-tolyl)prop-1-enyl)benzoate as a cream-coloured solid (9.8 g).

A solution of the foregoing ester (1.34 g) in ethanol (8 ml) and 2N-sodium hydroxide solution (3 mL) was stirred at room temperature for 3 hours. After addition of 2N-hydrochloric acid (3 mL) the solution was evaporated to dryness. The residue was extracted with boiling ethanol (2×20 mL) to leave an insoluble residue which was washed with water to leave 3-(3-pyrrolidino-1-(4-tolyl)-prop-12-enyl)benzoic acid (300 mg) crystallizing from methanol in colourless needles, m.p. 238°–240° (decomp) (hydrochloride, m.p. 205°–207°). The ethanol extract was evaporated to dryness and the residue was recrystallized from methanol to give colourless prisms (285 mg), m.p. 210°–215° (deomp.), of 3-(3-pyrrolidino-1-(4-tolyl)prop-1E-enyl)benzoic acid (hydrochloride, m.p. 180°–182°). Further amounts of the individual isomers were obtained by appropriate recrystallization of the residue from the filtrate.

EXAMPLE 2

(E)-3-(3-Pyrrolidino-1-(4-tolyl)prop-1E-enyl)cinnamic acid

To a stirred suspension of lithium aluminium hydride (330 mg) in ether (62 mL) was added methyl 3-(3-pyrrolidino-1-(4-tolyl)prop-1-enyl)benzoate (mixture of (E) and (Z)-isomers) (Example 1) and the mixture was refluxed for 6 hours. Water (0.33 mL) was added, followed by sodium hydroxide solution (15%, 0.33 mL) and finally water (1 mL), and the solid was filtered off and washed with ether. The ether filtrate was evaporated to give an oil (4.1 g) which when cooled in solution in a mixture of ether and light petroleum (b.p. 40°–60°) deposited crystals (1.43 g); recrystallization from light petroleum (b.p. 60°–80°) gave pure 3-(3-pyrrolidino-1-(4-tolyl)prop-1E-enyl)benzyl alcohol as colourless needles, m.p. 96°–97°. The ether-light petroleum filtrate was evaporated and the residue was separated by high performance liquid chromatography (silica, dichloromethane:methanol:triethylamine 98.5:1.25:0.25) to give more of the above (E)-isomer and also 3-(3-pyrrolidino-1-(4-tolyl)prop-1Z-enyl)benzyl alcohol which formed colourless prisms, m.p. 67°–69°, from light petroleum (b.p. 60°–80°).

To a stirred solution of the above 3-(3-pyrrolidino-1-(4-tolyl)-prop-1E-enyl)benzyl alcohol (1.1 g) in dichloromethane (75 mL) was added barium manganate (Firouzabadi and Ghaderi, *Tetrahedron Letters*, 1978, 839) and the mixture was kept at 40° for 7 hours, and left at room temperature for 16 hours. The solid was removed by filtration and the filtrate was evaporated to give the crude 3-(3-pyrrolidino-1-(4-tolyl)prop-1E-enyl)benzaldehyde (1.09 g) which was not further purified. To a stirred suspension of sodium hydride (107 mg; 80% oil suspension) in 1,2-dimethoxyethane (3.7 mL) was added diethyl methoxycarbonylmethyl-phosphonate (740 mg) in 1,2-dimethoxyethane (3.7 mL). After 15 minutes' stirring, a solution of the above (E)-aldehyde (1.09 g) in 1,2-dimethoxyethane (3.7 mL) was added dropwise and the mixture was stirred for 18 hours at room temperature. After addition of water and acidification with dilute hydrochloric acid, the suspension was washed with ether, and the clear aqueous solution was basified with sodium carbonate solution and the precipitated oil was extracted into ether. The washed and dried ether solution was evaporated to leave a solid (800 mg) which was dissolved in ethanol and refluxed with Girard reagent P (200 mg) for 1 hour. The solvent was evaporated, water and ether were added and the ether extract was washed, dried and evaporated to leave methyl (E)-3-(3-pyrrolidino-1-(4-tolyl)prop-1E-enyl)-cinnamate, m.p. 102°–107° (620 mg).

This ester (620 mg) was dissolved in ethanol (7 ml), 2N-sodium hydroxide solution (2.85 mL) was added and the mixture was stirred for 4 hours at room temperature. 2N-Hydrochloric acid (2.85 mL) was added and the solution was evaporated to dryness. Extraction of the solid residue with ethanol, and evaporation of the filtered extract, yielded a solid (600 mg) which was recrystallized from aqueous isopropanol to give light tan-coloured plates, m.p. 190° (decomp.), of (E)-3-(3-pyrrolidino-1-(4-tolyl)prop-1E-enyl)cinnamic acid. The compound formed a hydrochloride, m.p. 240°–245° (decomp.).

EXAMPLE 3

(E)-3-(3-Pyrrolidino-1-(4-methoxyphenyl)prop-1E-enyl)cinnamic acid

A mixture of 3-bromo-4'-methoxybenzophenone (Allen, Schumann, Day and Van Campen, *J. Amer. Chem. Soc.*, 1958, 80, 591) (14.6 g), ethyl acrylate (25.3 g), palladium (II) acetate (100 mg), triphenylphosphine (225 mg) and triethylamine (2.65 g) in acetonitrile (20 mL) was heated in a stainless steel autoclave under a nitrogen atmosphere at 155° for 5 hours. After cooling, water was added and the precipitated solid was recrystallized from methanol to yielded ethyl 3-(4-methoxy benzoyl)cinnamate, m.p. 71°–71.5° (5.6 g).

The foregoing ketone (3.1 g) reacted with the phosphorate derived from triphenyl 2-pyrrolidinoethylphosphonium bromide (4.4 g) under the conditions described in Example 1 to give a crude mixture of the (E)- and (Z)-forms of ethyl 3-(3-pyrrolidino-1-(4-methoxyphenyl)prop-1-enyl)cinnamate (4.3 g).

This crude ester mixture was hydrolyzed with aqueous ethanolic sodium hydroxide solution as described in Example 1 to give the mixed carboxylic acids. The mixture was separated by repeated crystallizations from ethanol or a mixture of methanol and ether to give (E)-3-(3-pyrrolidino-1-(4-methoxyphenyl)prop-1Z-enyl)cinnamic acid as small colourless prisms, m.p. 215°–220° (decomp.), and (E)-3-(3-pyrrolidino-1-(4-methoxyphenyl)prop-1E-enyl)cinnamic acid as colourless needles, m.p. 220°–225° (decomp).

EXAMPLE 4

(E)-3-(3-Dimethylamino)-1-(4-tolyl)prop-1E-enyl) cinnamic acid

By use of the methods described in Example 3,3-bromo-4'-methyl benzophenone (Ipatieff and Friedman, *J. Amer. Chem. Soc.*, 1939, 61, 684) was converted into ethyl 3-(4-toluoyl)cinnamate, m.p. 86°–87°, and thence into a mixture of the (E)- and (Z)-isomers of ethyl 3-(3- dimethylamino-1-(4-tolyl)prop-1-enyl)cinnamate. Hydrolysis of this ester mixture and separation of the mixture of carboxylic acids by crystallization yielded (E)-3-(3-dimethylamino-1-(4-tolyl)prop-1E-enyl)cinnamic acid, m.p. 200°–205° C., and (E)-3-(3-dimethylamino-1-(4-tolyl)prop-1Z-enyl)cinnamic acid, m.p. 200°–205° C.

EXAMPLE 5

3-(3-(3-Pyrrolidino-1-(4-tolyl)prop-1E-enyl)phenyl)-propionic acid.

Ethyl 3-(4-toluoyl)cinnamate (Example 4) (3.0 g), in solution in ethyl acetate (90 mL) was shaken with hydrogen in the presence of Raney nickel catalyst until slightly more than 1 molar equivalent of hydrogen had been absorbed. After removal of the catalyst by filtration, the residue was dissolved in dichloro-methane (200 mL), barium manganate (14 g) was added and the mixture was stirred at 50° for 2 hours. The filtered solution was evaporated to leave pure ethyl 3-(3-(4-toluoyl)-phenyl)propionate as a yellow oil. (A portion hydrolysed with dilute aqueous alcoholic sodium hydroxide gave the corresponding carboxylic acid, m.p. 137°–138.5°).

By the methods described in Example 3, the foregoing keto-ester was converted, by way of the mixture of isomers of ethyl 3-(3-(3-pyrrolidino-1-(4-tolyl)-prop-1-enyl)phenyl)propionate, into 3-(3-(3-pyrrolidino-1-(4-tolyl)prop-1E-enyl)phenyl)propionic acid, m.p. 138°–140° C., and 3-(3-pyrrolidino-1-(4-tolyl)prop-Z-enyl)phenyl)propionic acid, which was not isolated in a pure form.

EXAMPLE 6

Antihistaminic Activity

In vitro antihistaminic activity: The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., Arch. Int. Pharmacodyn. Ther. 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., Br. J. Pharmacol. 14, 48–58, 1959). Regression of Log (dr-1) on Log [B], where dr is an equiactive response in the presence and absence of antagonist and [B] is the molar concentration of antagonist, allowed an estimate of $pA_2$, i.e., the negative log of the concentration of antagonist which shifts the control histamine concentration-response curve 2X to the right.

TABLE I

Results of Antihistamine Assays

| Compound | $PA_2$ |
|---|---|
| 3-(3-pyrrolidino-1-(4-tolyl)prop-1E—enyl)benzoic acid | 8.1 |
| (E)—3-(3-pyrrolidino-1-(4-tolyl)prop-1E—enyl) cinnamic acid | 8.8 |
| (E)—3-(3-pyrrolidino-1-(4-methoxyphenyl)prop-1E—enyl)) cinnamic acid | 7.8 |
| (E)—3-(3-dimethylamino-1-(4-tolyl)prop-1E—enyl)) cinnamic acid | 6.9 |
| 3-(3-pyrrolidino-1-(4-tolyl)prop-1E—enyl)phenyl) propionic acid | 6.8 |

EXAMPLE 7

Formulations

| (A)-Injection | |
|---|---|
| Ingredient | Amount per ampoule |
| Compound of formula (I) | 1.0 mg |
| Water for Injections, q.s. | 1.0 mL |

The finely ground active compound is dissolved in the water for Injections. The solution is filtered and sterilized by autoclaving.

| (B)-Suppository | |
|---|---|
| Ingredient | Amount per suppository |
| Compound of Formula (I) | 1.0 mg |
| Cocoa Butter, or Wecobee ™ Base q.s. | 2.0 g |

Wecobee is a trademark and is a hydrogenated fatty carboxylic acid.

The finely ground active compound is mixed with the melted suppository base (either Cocoa Butter or Wecobee ™ base), poured into molds and allowed to cool to afford the desired suppositories.

| (C)-Syrup | |
|---|---|
| Ingredient | Amount per 5 mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water q.s. to | 5.0 mL |

Ethanol, sucrose, sodium benzoate, methylparaben, and flavouring are combined in 70% of the total batch quantity of water. Coloring and the active compound are dissolved in the remaining water, then the two solutions are mixed and clarified by filtration.

| (D)-Tablet | |
|---|---|
| Ingredient | Amount per Tablet |
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |
| Magnesium Stearate | 5.0 |

The finely ground active compound is mixed with the powdered excipients lactose, corn starch and stearic acid and packed into gelatin capsules.

| (F)-Tablet | |
|---|---|
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet is prepared from the above formulation by the method previously described in Example 7 (D).

| (G)-Syrup | |
|---|---|
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |
| Color | q.s. |
| Glycerol | 500 mg |
| Sucrose | 2000 mg |
| Purified Water q.s. to | 5.0 mL |

A syrup containing other active ingredients in addition to a compound of formula (I) is prepared from the above ingredients by an analogous method to that described for Example 7 (C) above.

| (H)-Nasal Spray | |
|---|---|
| Ingredient | Amount per 100.0 mL |
| Compound of Formula (I) | 1 g |
| Sodium Chloride | 0.8 g |
| Preservative | 0.5 g |
| Purified Water q.s. | 100.0 mL |

The preservative is dissolved in warm purified water and after cooling to 25°–30° C. the sodium chloride and the compound of formula (I) are added. The pH is then adjusted to 5.5–6.5 and purified water is added to bring the final volume to 100.0 mL.

| (I)-Ophthalmic Solution | |
|---|---|
| Ingredient | Amount per 100.0 mL |
| Compound of Formula (I) | 0.1 g |
| Sodium Chloride | 0.8 g |
| Preservative | 0.5 g |
| Water for Injection q.s. | 100.0 mL |

This formulation is prepared in a similar way to the nasal spray.

| (J)-Topical Cream | |
|---|---|
| Ingredient | Amount per 100.0 mL |
| Compound of Formula (I) | 0.1 g |
| Emulsifying Wax, N.F. | 15.0 g |
| Mineral Oil | 5.0 g |
| White Petrolatum | 5.0 g |
| Preservative | 0.25 g |
| Purified Water q.s. | 100 g |

The preservative is dissolved in approximately 50 g of warm purified water and after cooling to about 25°–30° the compound of formula (I) is added. In a separate container the emulsifying wax, mineral oil and white petrolatum are mixed well and heated to approximately 70°–80° C. The aqueous solution containing the compound of formula (I) is added to the warm mixture of emulsifying wax, mineral oil and petrolatum with vigorous mixing while cooling to 25° C. Additional purified water is added with mixing to bring the total amount to 100.0 g.

| (K)-Topical Lotion | |
|---|---|
| Ingredient | Amount per 100.0 mL |
| Compound of Formula (I) | 1.0 g |
| Carbomer, N.F. | 0.15 g |
| Triethanolamine | 0.15 g |
| Preservative | 0.5 g |
| Propyleneglycol | 5.0 g |
| Purified Water q.s. | 100 g |

The preservative is dissolved in approximately 50 g of warm purified water and after this solution is cooled to 25°–30° C., the compound of formula (I) is added. The carbomer is mixed in next followed by triethanolamine and propyleneglycol. Purified water was added to bring the total amount to 100 g and the formulation was mixed well.

We claim:

1. A compound of the formula (I)

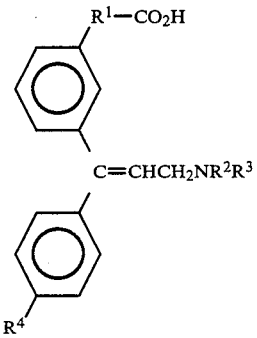

a straight or branched lower alkyl ester or a pharmaceutically acceptable salt thereof, wherein $R^1$ is $(CH_2)_n$ where n is an interger 0 to 7, or $(CH_2)_a CH{=}CH{-}(CH_2)_b$, a and b are independently 0 to 5 and the sum of a and b does not exceed 5; $R^2$ and $R^3$ are the same or different and are hydrogen, $C_{1-4}$ alkyl or taken together with nitrogen are pyrrolidino, piperidino or morpholino and $R^4$ is hydrogen, halogen, lower alkyl or lower alkoxy.

2. A compound which is 3-(3-pyrrolidino-1-(4-tolyl)-prop-1E-enyl)benzoic acid.

3. A compound which is (E)-3-(3-pyrrolidino-1-(4-methoxyphenyl)prop-1E-enyl))cinnamic acid.

4. A compound which is (E)-3-(3-dimethylamino-1-(4-tolyl)prop-1-E-enyl))cinnamic acid.

5. A compound which is 3-(3-(3-pyrrolidino-1-(4-tolyl)prop-1-E-enyl)phenyl))propionic acid.

6. A compound of which is (E)-3-(3-pyrrolidino-1-(4-tolyl)prop-1E-enyl)cinnamic acid.

7. The compound of claim 1 wherein $R^1$ is a bond, $(CH_2)_2$ or $CH{=}CH$, $NR^2R^3$ is pyrrolidino or dimethylamino.

8. A pharmaceutically acceptable salt of the compound of claim 2.

9. A pharmaceutically acceptable salt of the compound of claim 3.

10. A pharmaceutically acceptable salt of the compound of claim 4.

11. A pharmaceutically acceptable salt of the compound of claim 5.

12. A pharmaceutically acceptable salt of the compound of claim 6.

* * * * *